(12) United States Patent
Ward et al.

(10) Patent No.: US 7,965,156 B2
(45) Date of Patent: Jun. 21, 2011

(54) CARBON NANOTUBE RESONATORS COMPRISING A NON-WOVEN FABRIC OF UNALIGNED NANOTUBES

(75) Inventors: Jonathan W. Ward, Fairfax, VA (US); Brent M. Segal, Woburn, MA (US)

(73) Assignee: Nantero, Inc., Woburn, MA (US)

( * ) Notice: Subject to any disclaimer, the term of this patent is extended or adjusted under 35 U.S.C. 154(b) by 279 days.

(21) Appl. No.: 12/065,854

(22) PCT Filed: Sep. 5, 2006

(86) PCT No.: PCT/US2006/034477
§ 371 (c)(1),
(2), (4) Date: Sep. 3, 2008

(87) PCT Pub. No.: WO2007/030423
PCT Pub. Date: Mar. 15, 2007

(65) Prior Publication Data
US 2010/0060383 A1    Mar. 11, 2010

Related U.S. Application Data

(60) Provisional application No. 60/714,389, filed on Sep. 6, 2005.

(51) Int. Cl.
*H03H 9/24* (2006.01)
*H03H 9/00* (2006.01)
*H03H 9/46* (2006.01)

(52) U.S. Cl. ........ 333/186; 977/724; 977/742; 977/750; 977/752; 977/932

(58) Field of Classification Search .................. 333/186; 977/724, 734, 742, 750, 752, 932, 936
See application file for complete search history.

(56) References Cited

U.S. PATENT DOCUMENTS
4,979,149 A    12/1990    Popovic et al.
(Continued)

FOREIGN PATENT DOCUMENTS
FR    2874126    2/2006
(Continued)

OTHER PUBLICATIONS

International Search Report and Written Opinion issued for corresponding International Patent Application No. PCT/US2006/034477.

(Continued)

*Primary Examiner* — Barbara Summons
(74) *Attorney, Agent, or Firm* — Wilmer Cutler Pickering Hale and Dorr LLP (57) ABSTRACT

Under one aspect, a resonator 400 includes a nanotube element 410 including a non-woven fabric of unaligned nanotubes and having a thickness, and a support structure 404 defining a gap 406 over which the nanotube element 410 is suspended, the thickness of the nanotube element 410 and the length of the gap 406 being selected to provide a pre-specified resonance frequency for the resonator 400 The resonator 400 also includes a conductive element 412 in electrical contact with the nanotube element 410, a drive electrode 408 in spaced relation to the nanotube element 410, and power logic in electrical contact with die at least one drive electrode 408 The power logic provides a series of electrical pulses at a frequency selected to be about the same as the pre-specified resonance frequency of the resonator 400 to the drive electrode 408 during operation of the resonator 400, such that the nanotube element 410 responds to the series of electrical pulses applied to the drive electrode 408 by making a series of mechanical motions at the resonance frequency of the resonator 400.

28 Claims, 6 Drawing Sheets

U.S. PATENT DOCUMENTS

| | | | |
|---|---|---|---|
| 6,100,109 A | 8/2000 | Melzner et al. | |
| 6,128,214 A | 10/2000 | Kuekes et al. | |
| 6,166,948 A | 12/2000 | Parkin et al. | |
| 6,256,767 B1 | 7/2001 | Kuekes et al. | |
| 6,314,019 B1 | 11/2001 | Kuekes et al. | |
| 6,423,583 B1 | 7/2002 | Avouris et al. | |
| 6,426,687 B1 | 7/2002 | Osborn | |
| 6,443,901 B1 | 9/2002 | Fraser | |
| 6,445,006 B1 | 9/2002 | Brandes et al. | |
| 6,548,841 B2 | 4/2003 | Frazier et al. | |
| 6,706,402 B2 | 3/2004 | Rueckes et al. | |
| 6,803,840 B2 | 10/2004 | Hunt et al. | |
| 6,809,462 B2 | 10/2004 | Pelrine et al. | |
| 6,919,592 B2 | 7/2005 | Segal et al. | |
| 6,919,740 B2 | 7/2005 | Snider | |
| 6,924,538 B2 | 8/2005 | Jaiprakash et al. | |
| 6,955,937 B1 | 10/2005 | Burke et al. | |
| 6,969,651 B1 | 11/2005 | Lu et al. | |
| 7,071,023 B2 * | 7/2006 | Bertin et al. | 438/99 |
| 7,157,990 B1 * | 1/2007 | Adam et al. | 333/186 |
| 7,579,618 B2 * | 8/2009 | Adam | 257/25 |
| 2002/0153583 A1 | 10/2002 | Frazier et al. | |
| 2002/0167374 A1 | 11/2002 | Hunt et al. | |
| 2004/0181630 A1 | 9/2004 | Jaiprakash et al. | |
| 2004/0238907 A1 | 12/2004 | Pinkerton et al. | |
| 2004/0253167 A1 * | 12/2004 | Silva et al. | 423/447.1 |
| 2005/0065741 A1 | 3/2005 | Segal et al. | |
| 2005/0068128 A1 | 3/2005 | Yip | |
| 2005/0081983 A1 | 4/2005 | Nakayama et al. | |
| 2006/0237799 A1 | 10/2006 | Lu et al. | |
| 2006/0278902 A1 | 12/2006 | Sun et al. | |

FOREIGN PATENT DOCUMENTS

| | | |
|---|---|---|
| GB | 2364933 A | 2/2002 |
| WO | WO-0048195 C2 | 8/2000 |

OTHER PUBLICATIONS

Avouris, P., "Carbon nanotube electronics," Carbon, 2002, vol. 40, pp. 429-445, Chemical physics 281.

Bradley, K. et al., "Flexible Nanotube Electronics," Nano Letters 2003, vol. 3, No. 10, 1353-1355

Dequesnes, Marc, "Calculation of pull-in voltages for carbon-nanotube-based nanoelectromechanical switches," Nanotechnology, Jan. 22, 2002, vol. 13, pp. 120-131.

Kaneto, K. et al., "Electrical conductivities of multi-wall carbon nanotubes," Synthetic Metals 103 (1999) 2543-2546.

Stadermann, M. et al., "Nanoscale study of conduction through carbon nanotube networks," Physical Review B 69, 201402(R) (2004) pp. 201402-1 to 201402-3.

* cited by examiner

CARBON NANOTUBE RESONATORS COMPRISING A NON-WOVEN FABRIC OF UNALIGNED NANOTUBES

CROSS REFERENCE TO RELATED APPLICATIONS

This application is a U.S. National Phase Application under 35 U.S.C. §371 of International Patent Application No. PCT/US2006/034477, filed Sep. 5, 2006, entitled "Carbon Nanotube Resonators," which claims the benefit under 35 U.S.C. §119(e) of U.S. Provisional Patent Application No. 60/714,389, filed Sep. 6, 2005 and entitled "Carbon Nanotube Resonators," the entire contents of each are incorporated herein by reference.

BACKGROUND

1. Technical Field

The present application relates generally to nanotube films, layers, and fabrics.

2. Discussion of Related Art

Resonators are useful in signal processing systems as well as other systems. Reduction in the size of a resonator enhances its resonant frequency and reduces its energy consumption. When used as sensors, higher resonant frequency can translate into heightened sensitivity. When used in wireless communications, higher frequency resonators enable higher frequency filters, oscillators, and mixers to be made.

Current state of the art technology utilizes on-chip MEMs resonators. The motivation of MEMs technology in wireless communications is as a replacement for off-chip bandpass filters constructed from relatively large quartz resonators. MEMs resonator technology entails the fabrication of suspended silicon structures that are manipulated by applying an electric field to the structure, causing the suspended beam to vibrate at a specific frequency. These suspended silicon structures are typically several microns in length, width and height and have demonstrated frequencies greater than several MHz. Such suspended, mechanically active structures allow applications in force microscopy, optical couplers, and stable oscillators and filters.

Individual bridged carbon nanotubes have been used in resonator systems. See Li., C. et al., "Single-walled carbon nanotubes as ultrahigh frequency nanomechanical resonators", Phys. Rev. B, 2003, Vol. 68, pp. 073405-1-073405-3, the entire contents of which are incorporated herein by reference. Other materials that are being investigated for use in micro- or nano-sized actuators include: aluminum nitride, silicon (both single crystal and polycrystalline), silicon nitride, gallium arsenide, and silicon carbide. Mechanical actuation and sensing in most of these materials relies on electrostatic, optical, or magnetomotive techniques, which suffer from poor coupling and implementation difficulties. The use of aluminum nitride allows for high resonance frequencies and piezoelectric actuation. See Cleland, A. N., et al, "Single-crystal aluminum nitride nanomechanical resonators", Appl. Phys. Lett. 2001 Vol. 79, No. 13, 2070-2072, the entire contents of which are incorporated herein by reference. There has been a growing requirement for smaller, cheaper, lower power and higher performing resonators for application in wireless communications and other applications.

SUMMARY

The present invention provides carbon nanotube resonators.

Under one aspect, a resonator includes a nanotube element including a non-woven fabric of unaligned nanotubes and having a thickness, and a support structure defining a gap over which the nanotube element is suspended, the thickness of the nanotube element and the length of the gap being selected to provide a pre-specified resonance frequency for the resonator. The resonator also includes a conductive element in electrical contact with the nanotube element; a drive electrode in spaced relation to the nanotube element; and power logic in electrical contact with the at least one drive electrode. The power logic provides a series of electrical pulses at a frequency selected to be about the same as the pre-specified resonance frequency of the resonator to the drive electrode during operation of the resonator, such that the nanotube element responds to the series of electrical pulses applied to the drive electrode by making a series of mechanical motions at the resonance frequency of the resonator.

One or more embodiments include one or more of the following features. The pre-specified resonance frequency of the resonator is between about 1 GHz and about 10 THz. At least one of the spaced relation between the drive electrode and the nanotube element and a composition of the drive electrode is selected to avoid electrical communication between the nanotube element and the drive electrode during operation. The spaced relation between the drive electrode and the nanotube element is selected to prevent the nanotube element from physically touching the drive electrode during operation. The drive electrode includes an electrically insulating layer on a top surface of the electrode, the top surface facing the nanotube element, and a conductive layer underneath the top layer, and wherein the electrically insulating layer prevents the nanotube element from physically and electrically contacting the conductive layer during operation. The spaced relation between the drive electrode and nanotube element is selected such that a van der Waals force between the drive electrode and the nanotube element is sufficiently weak as to prevent non-volatile contact between the drive electrode and the nanotube element during operation. The nanotubes in the non-woven fabric move substantially as a single unit during operation. The nanotube element includes a multilayer nanotube fabric. The multilayer nanotube fabric has a thickness between about 10 nm and about 500 nm. The nanotube element includes substantially a monolayer of nanotubes. The nanotube element includes single-walled nanotubes. The nanotube element includes multi-walled nanotubes. The conductive element clamps the nanotube element to at least a portion of the support structure. The power source is further programmed to provide electrical stimulus to the conductive element. The electrical stimulus includes a substantially static charge. The electrical stimulus includes a second series of electrical pulses having a frequency selected to be about the same as the pre-specified resonance frequency of the resonator. The second series of electrical pulses has a phase that is offset from a phase of the previously mentioned series of electrical pulses. The phase offset is about 180 degrees. Further including a second conductive element in electrical contact with the nanotube element and in spaced relation to the first conductive element. The previously mentioned and second conductive elements clamp the nanotube element on either side of the gap. The conductive element includes metal. Further including a second drive electrode in spaced relation to the nanotube element and on an opposite side of the nanotube element from the previously mentioned drive electrode. The power source is further programmed to provide an electrical stimulus to the second drive electrode. The electrical stimulus includes a second series of electrical pulses having a frequency selected to be about the same as the pre-specified resonance frequency of the resonator. The second series of electrical pulses has a phase that is offset from a phase of the previously mentioned series of electrical pulses. The phase offset is about 180 degrees. Further including a self-assembled monolayer disposed on the drive electrode, the self-assembled monolayer selected to prevent the nanotube element from physically touching the drive electrode during operation. At least a portion of the nanotubes of the nanotube element are functionalized such that a van der Waals force between the drive electrode and the nanotube element is sufficiently weak as to prevent non-volatile contact between the drive electrode and the nanotube element during operation.

BRIEF DESCRIPTION OF THE DRAWING

In the Drawing,
FIGS. 1A and B illustrate nanotube based fabrics.

DETAILED DESCRIPTION

Carbon nanotubes (CNTs) have been shown to possess interesting electrical and mechanical properties that make them ideal for utilization as high frequency resonators in communications. Preferred embodiments of the present invention include the construction of individual resonators and arrays of resonators employing nanotube fabric elements made with standard CMOS and SOI integration techniques. Such resonators can be used as band pass filters for communications technology, among other things. A multilayered CNT fabric typically resonates in the millimeter wave length with frequencies greater than one GHz with a high Q-factor (e.g., >2400) and low power consumption. One advantage of CNT resonators compared to Micro-Electro-Mechanical (MEMS) resonators and quartz resonators is that CNT nanofabric based resonators can be created reliably in the sub 100 nm scale range. Such resonators can be used in ultra-small wireless communication electronics. Because the resonators of the present invention can be fabricated in current CMOS facilities, it is possible to construct arrays of filters on a single device, which can be tuned for specific frequencies, using current CMOS technology and current lithographic techniques.

Carbon nanotubes, specifically Single Walled Nanotubes (SWNTs), possess many interesting properties for electronics and integrated circuits. The electrical, mechanical, structural, chemical and optical properties of SWNTs can be utilized for fabrication of a variety of nanoelectronic devices. Examples include, but are not limited to, non-volatile random access memory (NRAM), one time programmable memory (OTP), light emitters, sensors, resistors and resonators. Because this large variety of different types of elements can be created on a single wafer simultaneously, improvements in electronics can be achieved using the fabric from the present invention and described in the incorporated patent references, which are given below.

Carbon nanotube-based fabric resonators can be useful in the integration of surface-acoustic wave devices on chip with silicon-based electronics. In addition, such a fabric can be used to fabricate submicron-scale cantilevers and flexural beams. The present resonators provide high-frequency nanoelectromechanical systems which can be used in new applications ranging from mechanical mass or charge detectors and nanodevices for high-frequency signal processing (e.g. to restrict unwanted signals from the rest of a given system) to biological imaging as well as the above-mentioned, force microscopy, optical couplers, and stable oscillators.

There has been a growing need for smaller, cheaper, lower power and higher performing resonators for application in wireless communications. These filters are employed to restrict unwanted signals from the rest of the system. Current state of the art technology utilizes on-chip MEMS resonators. The development of MEMS technology in wireless communications has generally been for the replacement of off-chip bandpass filters constructed from relatively large quartz resonators. MEMS resonator technology involves the fabrication of suspended silicon structures that are manipulated by applying an electric field to the structure, causing the suspended beam to vibrate at a specific frequency. These suspended silicon structures are typically several microns in length, width and height and have demonstrated frequencies greater than several MHz.

The frequency ($f_r$) at which a suspended rigid structure vibrates is determined by Equation 1, where $K_r$ is the beam stiffness, $m_r$ is the mass of the beam, E is the Young's modulus of the beam, $\rho$ is the beam material's density, h is the thickness of the beam and $L_r$ is the length of the suspended region of the beam.

$$f_r = \frac{1}{2\pi}\sqrt{\frac{K_r}{m_r}} = 1.03\sqrt{\frac{E}{\rho}}\frac{h}{L_r^2} \qquad \text{Equation 1}$$

Equation 1 predicts that a material with a higher stiffness or modulus will resonate at higher frequencies. Also evident is that a beam with a smaller mass or density will also resonate at higher frequencies. The pull-down voltage ($V_{pd}$), (i.e. the voltage required to deflect the suspended beam until it makes contact with the charged electrode), is calculated by employing Equation 2, where $\epsilon_0$ is the permittivity of free space, d is the gap height, $W_r$ is the width of the suspended beam and $W_{el}$ is the width of the electrode.

$$V_{pd} = \sqrt{\frac{8K_r d^3}{27\epsilon_0 W_r W_{el}}} \qquad \text{Equation 2}$$

As can be seen from Equation 2, as the stiffness of the resonator beam and the gap height between the beam and the electrode increases, larger pull-down voltages are generally required. During typical operation, the resonator will not physically and/or electrically contact the charged electrode. Contact (particularly nonvolatile contact) between the suspended beam and the electrode may prevent resonator vibration because of the van der Waals forces not allowing the beam to release from the electrode.

Employing CNTs as the suspended resonator material allows the fabrication of nanometer-sized bandpass filters that operate in the GHz to THz range with very small power consumption. Carbon nanotubes, specifically single walled nanotubes (SWNTs), posses a very high Young's Modulus (~1 TPa) and have a small density (1.33-1.4 g/cm$^3$). For example, a 50 nm thick CNT fabric, which is 200 nm long, will exhibit a resonant frequency of the order of several GHz (as determined using Equation 1, above). SWNTs are also able to withstand high elastic strains without plastic deformation or fracture. Other valuable and unique properties that make CNT resonators useful as bandpass filters include their electrical characteristics (where depending on their diameter and helicity, SWNTs behave as either one-dimensional metals or semiconductors), their optical properties and their extremely high thermal conductivities (e.g., on the order of 6600 W/cm$^2$s). It is also possible to expose the CNTs to various corrosive and reductive atmospheres without any degradation in the properties of the CNTs because the nanotubes are typically chemically inert. The combination of these unique properties enables the construction of ultra-small wireless communication electronics that operate up to the millimeter wave range.

Figure 1A:
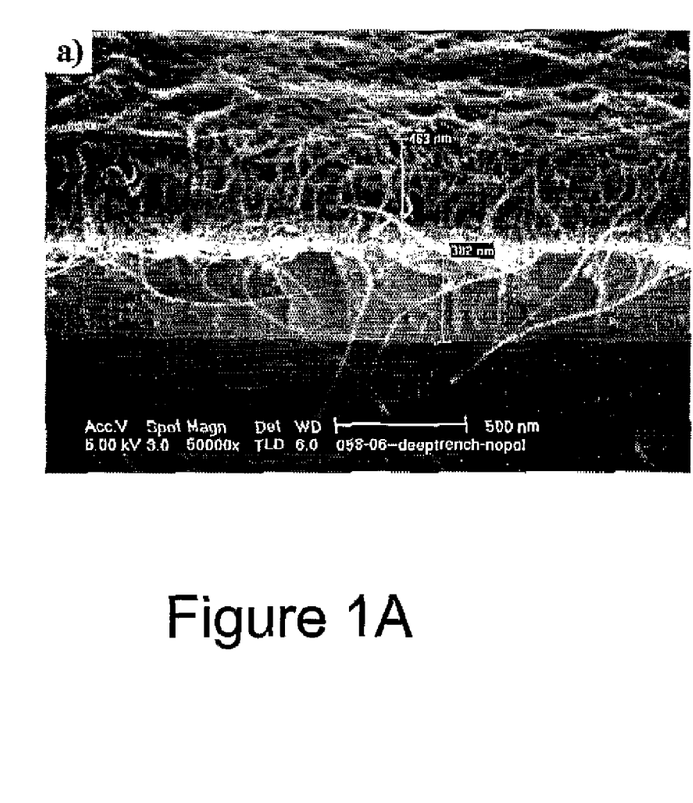
Figure 1B:
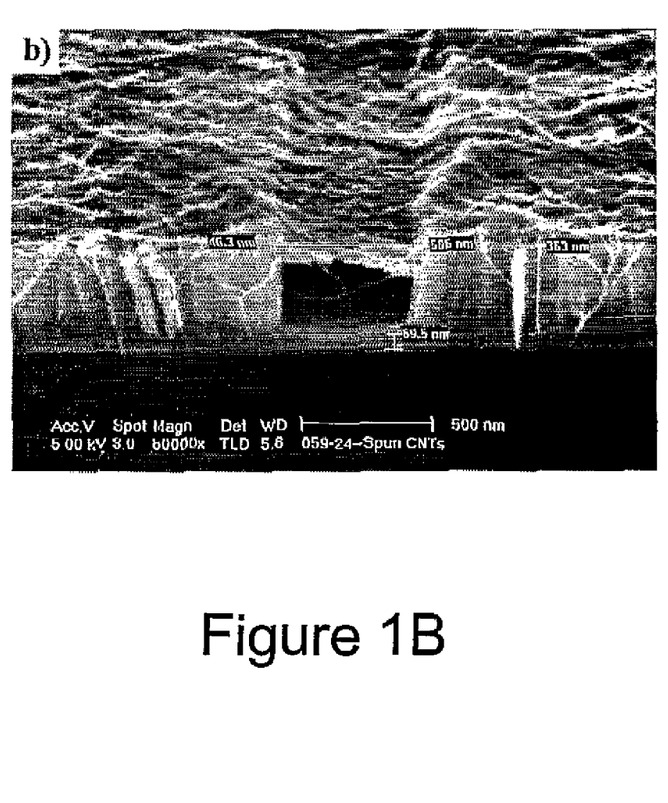

FIG. 1A shows an embodiment of a relatively thick CNT fabric (greater than about 450 nm) deposited on a flat surface. The fabric has a porosity of about 80%, and was created by spray coating the CNTs onto the substrate. CNT fabrics can be made with a variety of other methods, as described, e.g., in the incorporated patent references. FIG. 1B illustrates an embodiment of a thinner multilayered fabric (about 45 nm) that is suspended over an open trench that is about 600 nm wide. Multilayered CNT fabrics typically have sheet resistance values that range anywhere from several Ohms to several hundreds of Ohms. The sheet resistance is related to the thickness of the fabric and how many metallic CNTs are in electrical contact with each other, within the multilayered fabric.

After the CNT fabric is deposited, the fabric can be patterned to make ribbons of SWNTs. Exemplary patterning techniques are described in the incorporated patent references.

Figure 2A:
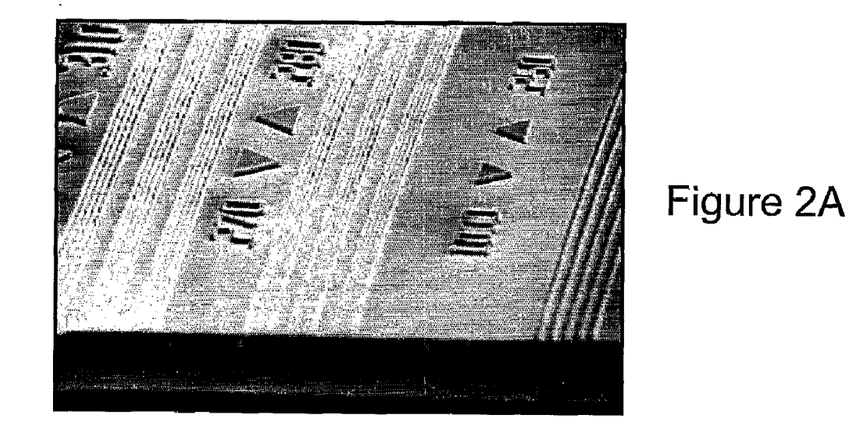
FIG. 2A illustrates the scale at which lithography may take place.
Figure 2B:
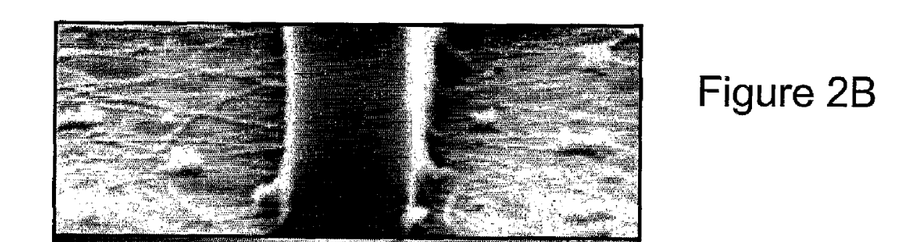
FIGS. 2B and C illustrate patterned nanofabric for use in the present invention.
Figure 2C:
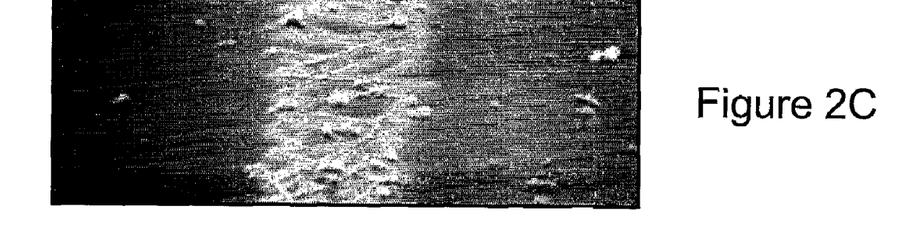

To pattern the fabric, a photoresist is spun onto the wafer that contains the CNTs. The photoresist is then exposed, producing the desired pattern in the photoresist. After exposure and any required bakes, the photoresist is developed. To transfer the pattern from the photoresist to the underlying CNT fabric, an oxygen ash is performed. When the fabric is exposed to a reactive oxygen atmosphere carbon-monoxide and carbon-dioxide are formed, creating the patterned CNT ribbon. The addition of other etching species such as fluorines or chlorines can be used in some instances when appropriate. FIG. 2A is an FESEM image showing the resolution of a photoresist pattern on top of an etched CNT fabric and FIG. 2B illustrates a 250 nm wide exposed photoresist pattern on top of a non-etched CNT fabric. FIG. 2C illustrates an etched CNT pattern with no remaining resist.

Once the CNT fabric has been patterned, further processing can then be performed without damaging the properties and characteristics of the patterned CNT fabric. The CNT fabric can than be exposed to various metal deposition methods, various etching methods and various corrosive and reductive atmospheres without any degradation of the CNT ribbon's properties.

Figure 3:
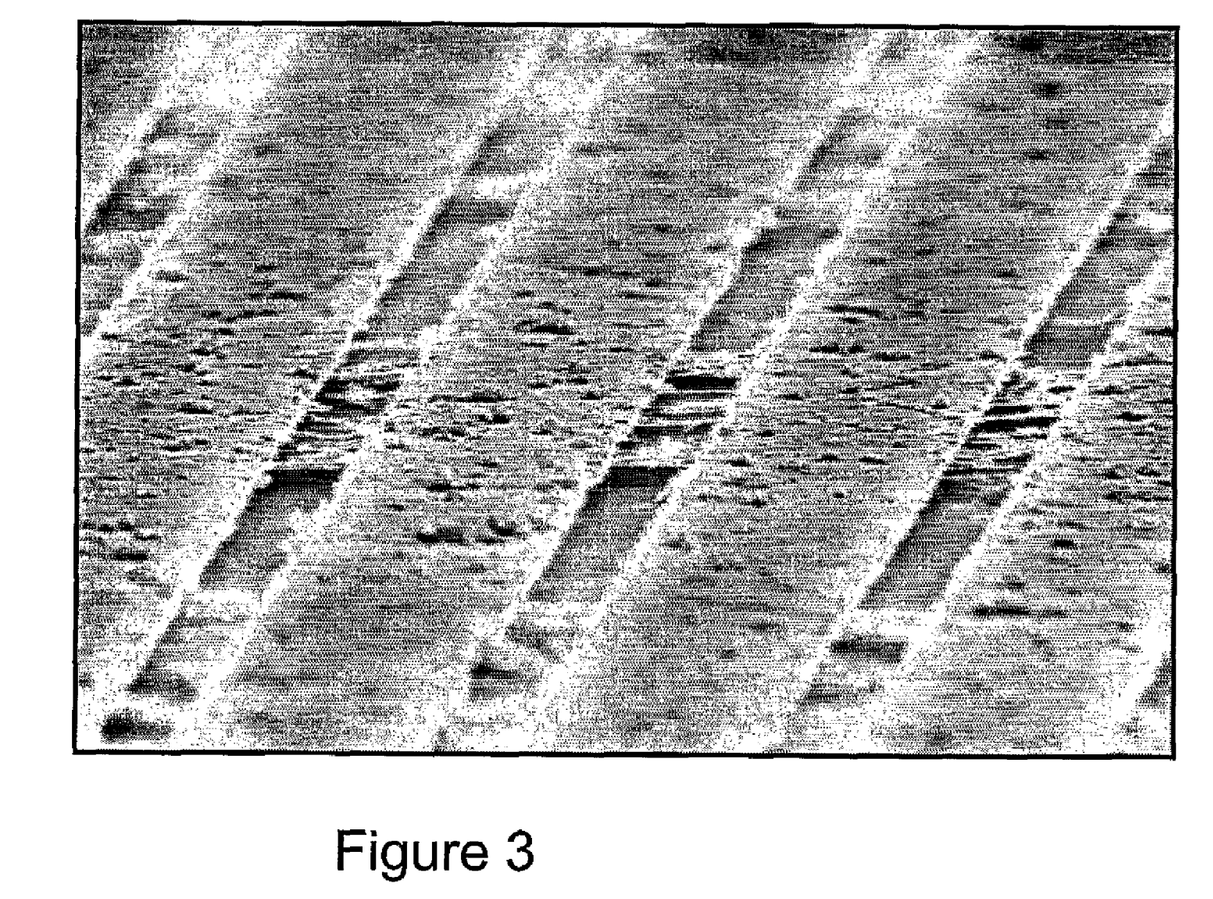
FIG. 3 is an FESEM micrograph of suspended nanotube fabric.

FIG. 3 shows a suspended patterned fabric that is clamped by metal, e.g., deposited over the nanotube fabric, running the length of the supports. (Note that this is a micrograph of an actual nanotube-based fabric which was patterned and subjected to several processing steps such as a 2$^{nd}$ lithography step, metal deposition, metal lift-off and a wet chemical etch to suspend the fabric without any noticeable degradation in the characteristics of the CNT fabric. Such steps are described in greater detail in the incorporated patent references.

The design of a CNT resonator is similar to the image displayed in FIG. 3. The resonator includes a suspended CNT fabric that is pinned/clamped/contacted by two contacts over a support structure that defines a gap. Typically, one or both of the contacts are metallic, though other conductive materials can be used. In certain embodiments, only one of the contacts is conductive. The CNT fabric will typically be a multilayer fabric, although monolayers could also be used. A drive electrode, which is in spaced relation to the CNT fabric, is used repeatedly to pull-down the CNT fabric and thus generate a resonance. The drive electrode is connected by a metal interconnect to power logic (not shown).

As shown in Equations 1 and 2, the resonance frequency of a resonator is a function of many variables. When designing a CNT resonator having a nanotube fabric, the variables that are typically adjusted in order to pre-specify the resonance frequency of the resonator include the thickness of the nanotube element, which generally provides a pre-selected "stiffness" and "mass" to the element, and the length of the gap over which the nanotube element is suspended. Other variables that can be adjusted include the density, and modulus of the nanotube fabric, which in some cases are varied by changing the nanotube composition (e.g., single-walled, multi-walled, metallic, semiconducting), and the density at which the nanotubes are applied.

In many embodiments, either the spacing between the drive electrode and the nanotube element, or the composition of the drive electrode is selected so as to avoid electrical communication between the nanotube element and the drive electrode during operation. For example, the spacing may be sufficient to substantially prevent the nanotube element from physically touching the drive electrode during operation. Typically, the spacing will be at least large enough that a van der Waals force between the drive electrode and the nanotube element sufficiently weak as to prevent non-volatile physical contact ("sticking") between the drive electrode and the nanotube element during operation. The drive electrode may also include a coating layer, e.g., an insulator layer or a self-assembled monolayer, over a conductive layer, where the coating layer faces the nanotube element. In this case, even if the nanotube element physically contacts the drive electrode, the coating layer prevents the nanotube element from physically and electrically contacting the conductive layer during operation. The coating layer may also or alternatively reduce a van der Waals attraction between the nanotube element and the drive electrode.

Figure 4A:
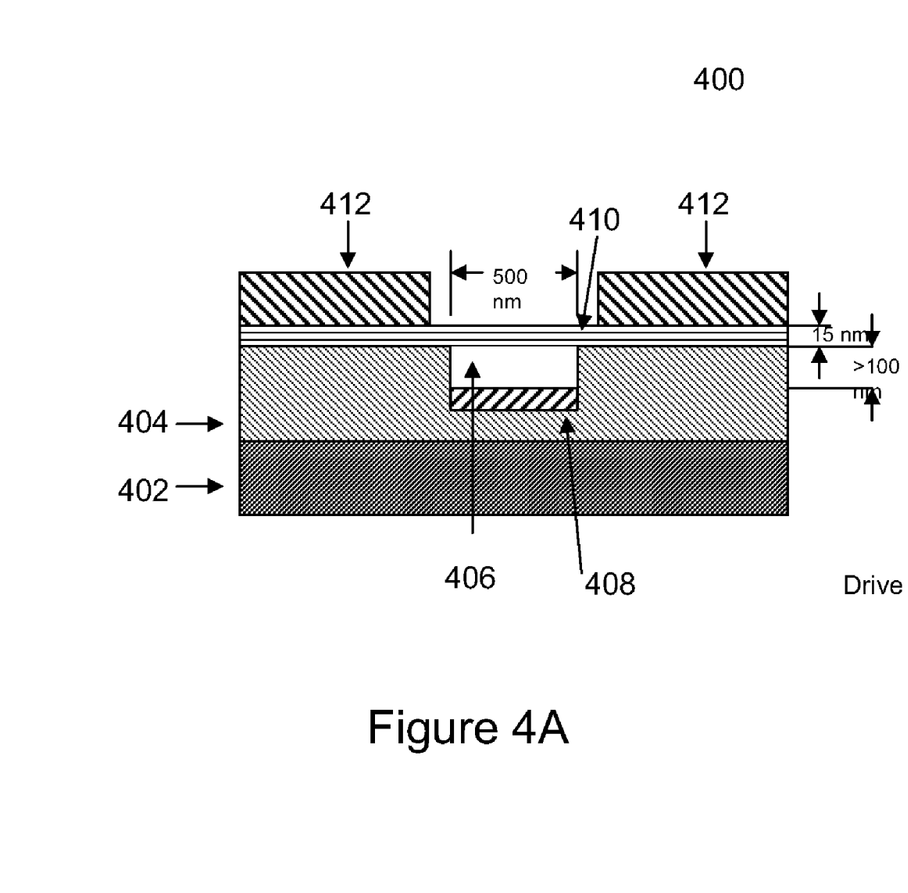
FIGS. 4A and B illustrate exemplary embodiments of the present invention.
Figure 4B:
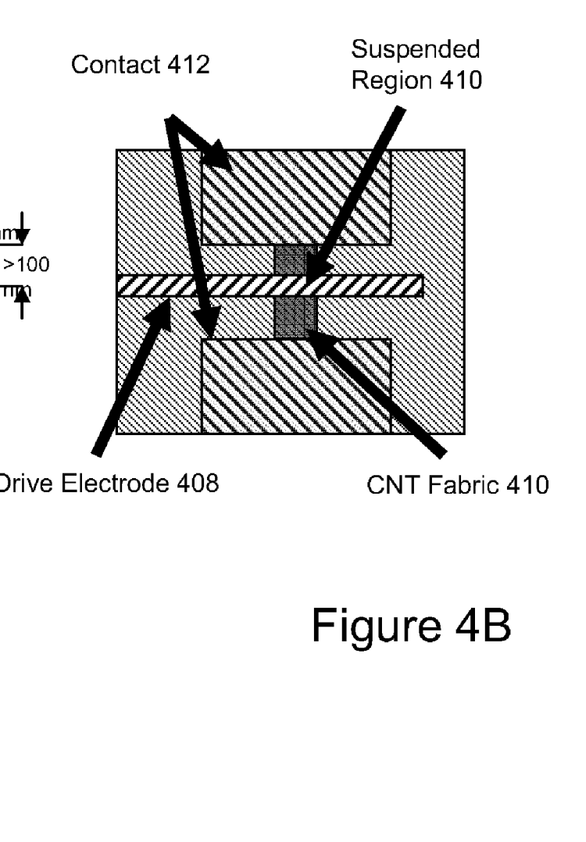

FIGS. 4A and 4B illustrate plan and side views, respectively, of one design for a simple CNT resonator device 400. A substrate 402 is situated below an insulator layer 404 having a gap 406 and a drive electrode 408 situated therein. Spanning the gap 406 is a suspended portion of nanotube fabric 410. The nanotube fabric 410 is electrically contacted by a contact layer 412. The length of the suspended region of the fabric can be varied from about hundreds of nanometers up to several microns; the suspended length of fabric, in part, determines the resonance frequency of the resonator.

While a monolayer fabric may be used, a multilayer fabric may also be used depending on desired resonance characteristics. The creation of fabrics of varying densities is more fully described in the incorporated patent references. In general, during operation, the CNTs within a multilayered fabric will act in unison as one single structure (analogous to a micron sized suspended silicon beam). One advantage to using a multilayered fabric is that longer trench lengths may be constructed, because the interaction between individual CNTs within the fabric will typically prevent the dangling and slacking of the nanotubes, which may otherwise cause one or more nanotubes to contact to the drive electrode, similar to twisted strands of rope, as may be the case with fabrics with very few layers and few nanotubes. The removal of dangling tubes may be attained, e.g. by a burn off procedure as described in the incorporated patent references. Multilayer CNT fabrics are also generally stiffer than monolayer fabrics because of the combined interaction of the large number of nanotubes as compared to a monolayered fabric.

Figure 5:
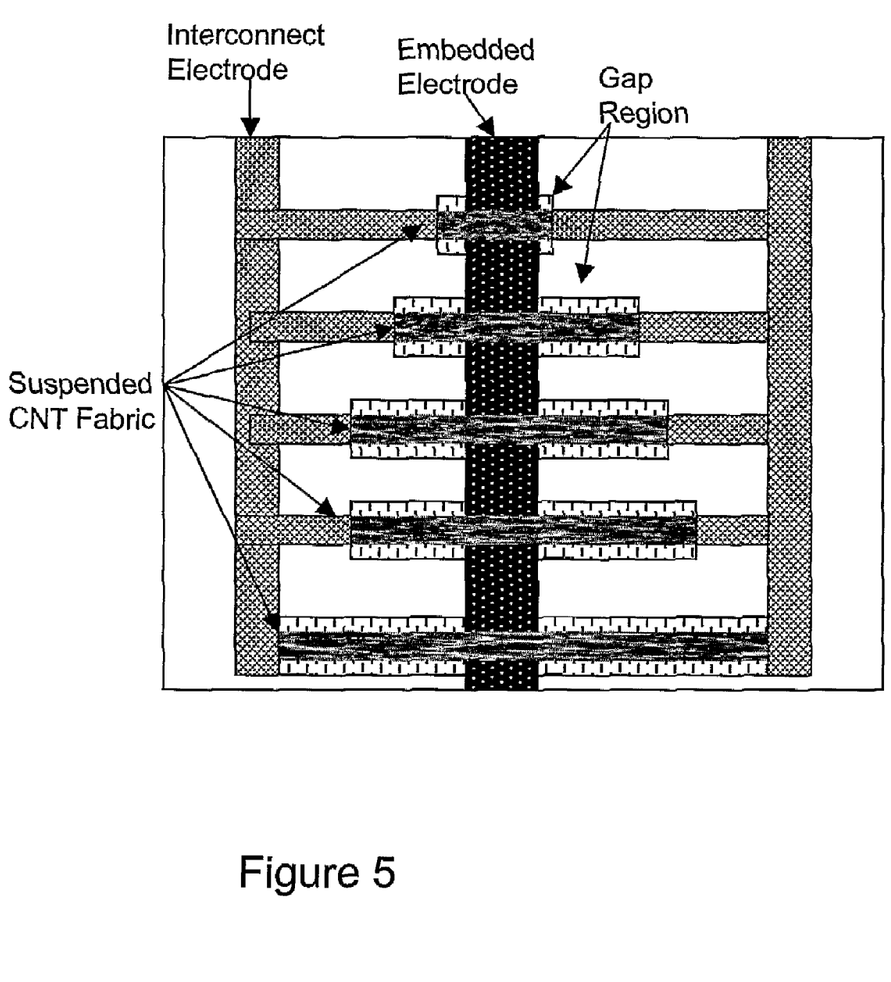
FIG. 5 illustrates an array of elements according to the present invention.

FIG. 5 is a plan view of an array of CNT based resonators fabricated simultaneously on a substrate. In this exemplary array, all of the patterned CNT fabrics contain the same thickness and gap height, however, the CNT suspension length can be varied to tailor the properties of the resonator. Similar devices can be constructed with varying gap heights and CNT thickness or a combination of all three variables. Compared to current Silicon MEMs technology and quartz resonators, the space required to fabricate the CNT resonators is much reduced. Quartz resonators require more than several square millimeters, while Si MEMs are usually several tens to hundreds of square microns in size. CNT resonators, however, can be fabricated at the current CMOS technology node, allowing for a large number of structures to be fabricated in a much smaller space; a smaller technology node results in a higher possible frequency response.

While not shown, CNT resonators may also be created which are clamped or pinned on one end of the nanofabric. The use of such singly-pinned resonators is similar to that of doubly-pinned resonators, however, specific operation of the differently constructed devices may vary.

Carbon nanotube resonators are believed to possess many advantages over current silicon based MEMS band-pass filters. The frequency response and pull-down voltage, as calculated using Equations 1 and 2, shows that a 500 nm long× 500 nm wide×50 nm high CNT fabric suspended 50 nm over a 500 nm wide embedded electrode will have a frequency response of the order of several THz with a pull-down voltage of several mV. Thus, CNT resonators are relatively high frequency devices with little power consumption during operation. In line with other MEMS resonators, the drastic decrease in size also causes a drastic increase in the Q-factor of the device.

The fabrication of CNT-based resonators is also generally compatible with silicon CMOS and SOI technology. As compared with silicon resonators, CNT based resonators can be built on various types of substrates (oxides, metals, glasses, etc.) and/or or at different integration levels of a CMOS chip (various metal levels). CNTs are also generally chemically inert, and thus will not typically react with their surroundings such as the substrate, contacts and operation atmosphere; therefore, the CNT fabric-based resonators typically need not be hermetically sealed or passivated. Silicon MEMS resonators are typically negatively affected by water and oxygen in their environments, while CNTs are not affected by oxygen atmospheres at temperatures below about 400° C.

CNTs are also inherently a radiation hard material; therefore, the CNT resonators of the present invention can be used in high radiation environments, such as in outer space with no appreciable degradation in performance.

The CNT resonator of the present invention is also not subjected to fatigue and brittle fracture due to the mechanical properties of the CNTs. Since CNTs can generally withstand large amounts of strain (e.g., up to about 20%) and have an extremely high tensile strength, failure issues such as fatigue and fracture will typically not limit the lifetime of the CNT resonator. Also, due to the nanometer sized dimensions, the effects of external shock and vibration will typically not cause extraneous electrical signals in the CNT filter, making the CNT resonators useful for space-based applications.

The CNT resonators of the present invention may be used in other applications such as mass spectroscopy, calorimetery and bolometry, for example, opening or closing valves in fluidic systems.

Because CNT fabrics can be readily made, and have useful properties, and also can be readily fabricated, e.g., in a CMOS fab, vast arrays of CNT resonators can be fabricated (e.g., the array in FIG. 5) with varying resonant frequencies which may be tailored to different specific needs. The resonators are capable of being mass-produced in current CMOS fabrication facilities. Large arrays of resonators of differing frequencies may be constructed on a single wafer, therefore multiple filters in a single active region with different frequency responses may be realized utilizing very few or even a single lithographic step. Arrays of differently-tuned nanofabric-based resonators of the present invention will require less space compared to current resonators fabricated using silicon MEMS technology or quartz resonators.

CNT resonators typically vibrate at frequencies of GHz to THz, depending on the properties and design of the suspended CNT fabric, as well as of the length of the suspended gap. Comparatively little power is consumed by CNT-based filters since only several milli-Volts are required to resonance in the multilayered nanotube fabric.

OTHER EMBODIMENTS

CNT resonators can also be constructed with more than one driving electrode. For example, a CNT fabric may be suspended between an upper and lower electrode, and one or both electrodes may be used to drive the resonator. For example, the electrodes may pulse alternately from each other, in approximate synchronization with the motion of the CNT fabric between them. Further, the surface of the driving electrode(s) may be coated with insulator material depending on the desired characteristics of the final product, so that even if the CNTs touch the electrode, electrical contact is not made and does not interfere with the operation of the device. Insulated electrodes are more fully described in the incorporated patent references as well as in U.S. patent application Ser. No. 11/264,935, the entire contents of which are incorporated herein by reference.

Figure 6A:
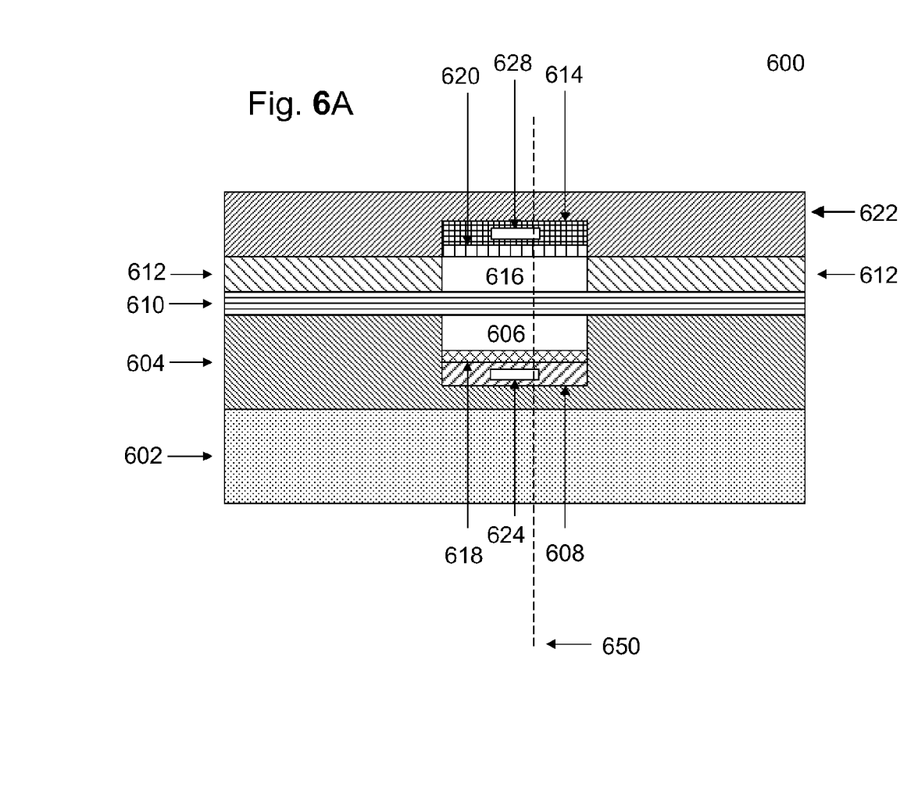
FIGS. 6A and 6B illustrate views of a CNT resonator according to embodiments of the present invention.
Figure 6B:
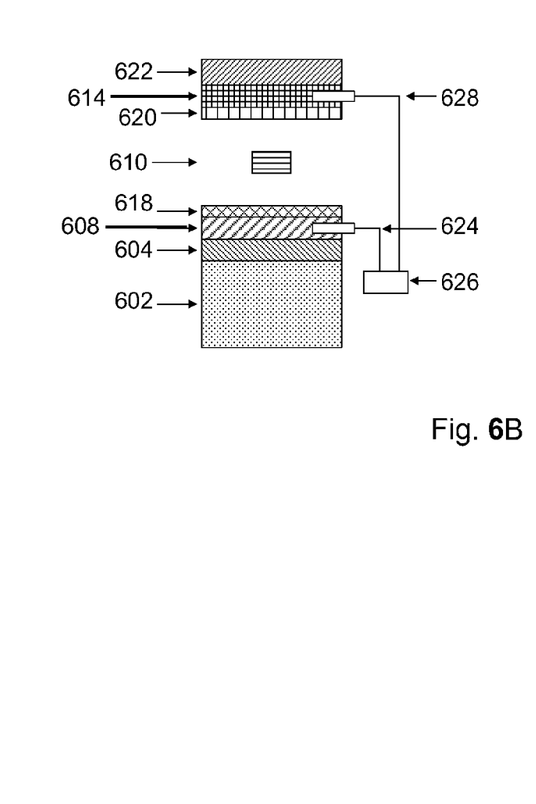

FIGS. 6A and 6B illustrate longitudinal cross-sectional and latitudinal cross-sectional side views, respectively, of one design for a CNT resonator device 600. FIG. 6B illustrates a cross section corresponding to dashed line 650 in FIG. 6A. A substrate 602 is situated below a first insulator layer 604 having a first gap 606 and a first drive electrode 608 situated therein. The first drive electrode 608 has an insulating layer 618 on the top surface of the electrode. Spanning the first gap 606 is a suspended portion of nanotube fabric 610. The nanotube fabric 610 is electrically contacted by a contact layer 612. A second drive electrode 614 is in spaced relation to the nanotube fabric 610 and is on an opposite side of the nanotube fabric 610, separated by a second gap 616 and situated below a second insulator layer 622. The second drive electrode 614 has a self-assembled monolayer 620 disposed on the electrode. The power logic 626 is in electrical contact with the first drive electrode 608 via interconnect 624. Power logic 626 is in electrical contact with the second drive electrode 614 via interconnect 628.

The following commonly-owned patent references, referred to herein as "incorporated patent references,"

describe various techniques for creating nanotube elements (nanotube fabric articles and switches), e.g., creating and patterning nanotube fabrics, and are incorporated herein by reference in their entireties:

U.S. patent application Ser. No. 09/915,093, Electromechanical Memory Array Using Nanotube Ribbons and Method for Making Same, filed Jul. 25, 2001, now U.S. Pat. No. 6,919,592;

U.S. patent application Ser. No. 09/915,173, Electromechanical Memory Having Cell Selection Circuitry Constructed with Nanotube Technology, filed Jul. 25, 2001, now U.S. Pat. No. 6,643,165;

U.S. patent application Ser. No. 09/915,095, Hybrid Circuit Having Nanotube Electromechanical Memory, filed Jul. 25, 2001, now U.S. Pat. No. 6,574,130;

U.S. patent application Ser. No. 10/033,323, Electromechanical Three-Trace Junction Devices, filed Dec. 28, 2001 now U.S. Pat. No. 6,911,682;

U.S. patent application Ser. No. 10/802,900, Electromechanical Three-Trace Junction Devices, filed Mar. 17, 2004;

U.S. patent application Ser. No. 10/033,032, Methods of Making Electromechanical Three-Trace Junction Devices, filed Dec. 28, 2001, now U.S. Pat. No. 6,784,028;

U.S. patent application Ser. No. 10/128,118, Nanotube Films and Articles, filed Apr. 23, 2002, now U.S. Pat. No. 6,706,402;

U.S. patent application Ser. No. 10/128,117, Methods of Nanotube Films and Articles, filed Apr. 23, 2002 now U.S. Pat. No. 6,835,591;

U.S. patent application Ser. No. 10/864,186, Non-Volatile Electromechanical Field Effect Devices and Circuits Using Same and Methods of Forming Same, filed Jun. 9, 2004, now U.S. Patent Publication No. 2005/0062035;

U.S. patent application Ser. No. 10/341,005, Methods of Making Carbon Nanotube Films, Layers, Fabrics, Ribbons, Elements and Articles, filed Jan. 13, 2003;

U.S. patent application Ser. No. 10/341,055, Methods of Using Thin Metal Layers To Make Carbon Nanotube Films, Layers, Fabrics, Ribbons, Elements and Articles, filed Jan. 13, 2003;

U.S. patent application Ser. No. 10/341,054, Methods of Using Pre-formed Nanotube Films, Layers, Fabrics, Ribbons, Elements and Articles, filed Jan. 13, 2003;

U.S. patent application Ser. No. 10/341,130, Carbon Nanotube Films, Layers, Fabrics, Ribbons, Elements and Articles, filed Jan. 13, 2003;

U.S. patent application Ser. No. 10/776,059, Electromechanical Switches and Memory Cells Using Horizontally-Disposed Nanofabric Articles and Methods of Making Same, filed Feb. 11, 2004;

U.S. patent application Ser. No. 10/776,572, Electromechanical Switches and Memory Cells Using Vertically-Disposed Nanofabric Articles and Methods of Making the Same, filed Feb. 11, 2004 now U.S. Pat. No. 6,924,538;

U.S. patent application Ser. No. 10/917,794, Nanotube-Based Switching Element, filed Aug. 13, 2004;

U.S. patent application Ser. No. 10/918,085, Nanotube-Based Switching Elements With Multiple Controls, filed Aug. 13, 2004;

U.S. patent application Ser. No. 10/936,119, Patterned Nanoscopic Articles and Methods of Making the Same, filed Sep. 8, 2004, now U.S. Patent Publication No. 2005/0128788; and U.S. patent application Ser. No. 11/398,126, Nanotube Articles with Adjustable Conductivity and Methods of Making the Same, filed Apr. 5, 2006.

It will be further appreciated that the scope of the present invention is not limited to the above-described embodiments, but rather is defined by the appended claims, and that these claims will encompass modifications of and improvements to what has been described.

What is claimed is:

1. A resonator, comprising:
   a nanotube element comprising a non-woven fabric of unaligned nanotubes and having a thickness, and
   a support structure defining a gap over which the nanotube element is suspended, the thickness of the nanotube element and the length of the gap being selected to provide a pre-specified resonance frequency for the resonator;
   a conductive element in electrical contact with the nanotube element;
   a drive electrode in spaced relation to the nanotube element; and
   power logic in electrical contact with the at least one drive electrode, the power logic providing a series of electrical pulses at a frequency selected to be about the same as the pre-specified resonance frequency of the resonator to the drive electrode during operation of the resonator, such that the nanotube element responds to the series of electrical pulses applied to the drive electrode by making a series of mechanical motions at the resonance frequency of the resonator.

2. The resonator of claim 1, wherein the pre-specified resonance frequency of the resonator is between about 1 GHz and about 10 THz.

3. The resonator of claim 1, wherein at least one of the spaced relation between the drive electrode and the nanotube element and a composition of the drive electrode is selected to avoid electrical communication between the nanotube element and the drive electrode during operation.

4. The resonator of claim 3, wherein the spaced relation between the drive electrode and the nanotube element is selected to prevent the nanotube element from physically touching the drive electrode during operation.

5. The resonator of claim 3, wherein the drive electrode comprises an electrically insulating layer on a top surface of the electrode, the top surface facing the nanotube element, and a conductive layer underneath the top layer, and wherein the electrically insulating layer prevents the nanotube element from physically and electrically contacting the conductive layer during operation.

6. The resonator of claim 1, wherein the spaced relation between the drive electrode and nanotube element is selected such that a van der Waals force between the drive electrode and the nanotube element is sufficiently weak as to prevent non-volatile contact between the drive electrode and the nanotube element during operation.

7. The resonator of claim 1, wherein the nanotubes in the non-woven fabric move substantially as a single unit during operation.

8. The resonator of claim 1, wherein the nanotube element comprises a multilayer nanotube fabric.

9. The resonator of claim 8, wherein the multilayer nanotube fabric has a thickness between about 10 nm and about 500 nm.

10. The resonator of claim 1, wherein the nanotube element comprises substantially a monolayer of nanotubes.

11. The resonator of claim 1, wherein the nanotube element comprises single-walled nanotubes.

12. The resonator of claim 1, wherein the nanotube element comprises multi-walled nanotubes.

13. The resonator of claim 1, wherein the conductive element clamps the nanotube element to at least a portion of the support structure.

14. The resonator of claim 1, wherein the power logic is further programmed to provide electrical stimulus to the conductive element.

15. The resonator of claim 14, wherein the electrical stimulus comprises a substantially static charge.

16. The resonator of claim 14, wherein the electrical stimulus comprises a second series of electrical pulses having a frequency selected to be about the same as the pre-specified resonance frequency of the resonator.

17. The resonator of claim 16, wherein the second series of electrical pulses has a phase that is offset from a phase of the previously mentioned series of electrical pulses.

18. The resonator of claim 17, wherein the phase offset is about 180 degrees.

19. The resonator of claim 1, further comprising a second conductive element in electrical contact with the nanotube element and in spaced relation to the first conductive element.

20. The resonator of claim 19, wherein the previously mentioned and second conductive elements clamp the nanotube element on either side of the gap.

21. The resonator of claim 1, wherein the conductive element comprises metal.

22. The resonator of claim 1, further comprising a second drive electrode in spaced relation to the nanotube element and on an opposite side of the nanotube element from the previously mentioned drive electrode.

23. The resonator of claim 22, wherein the power logic is further programmed to provide an electrical stimulus to the second drive electrode.

24. The resonator of claim 23, wherein the electrical stimulus comprises a second series of electrical pulses having a frequency selected to be about the same as the pre-specified resonance frequency of the resonator.

25. The resonator of claim 24, wherein the second series of electrical pulses has a phase that is offset from a phase of the previously mentioned series of electrical pulses.

26. The resonator of claim 25, wherein the phase offset is about 180 degrees.

27. The resonator of claim 1, further comprising a self-assembled monolayer disposed on the drive electrode, the self-assembled monolayer selected to prevent the nanotube element from physically touching the drive electrode during operation.

28. The resonator of claim 1, wherein at least a portion of the nanotubes of the nanotube element are functionalized such that a van der Waals force between the drive electrode and the nanotube element is sufficiently weak as to prevent non-volatile contact between the drive electrode and the nanotube element during operation.

* * * * *